United States Patent [19]
Fowler

[11] Patent Number: 5,387,201
[45] Date of Patent: Feb. 7, 1995

[54] EYE SURGERY IRRIGATION DEVICE

[76] Inventor: Bernard J. Fowler, 216 Engle St., Englewood, N.J. 07631

[21] Appl. No.: 238,894

[22] Filed: May 6, 1994

[51] Int. Cl.⁶ ............................................. A61M 7/00
[52] U.S. Cl. ................................... 604/290; 604/294
[58] Field of Search ............... 604/30, 294, 295, 296, 604/297, 298, 300, 290

[56] References Cited

U.S. PATENT DOCUMENTS

| | | |
|---|---|---|
| 1,152,818 | 9/1915 | Kells . |
| 2,633,122 | 3/1953 | Vannas ........................ 604/294 X |
| 4,131,115 | 12/1978 | Peng ............................. 604/297 |
| 4,193,401 | 3/1980 | Marinello ...................... 604/294 X |
| 4,679,551 | 7/1987 | Anthony . |
| 4,758,237 | 7/1988 | Sacks ............................. 604/297 |
| 4,798,599 | 1/1989 | Thomas . |
| 4,892,526 | 1/1989 | Reese . |
| 5,030,214 | 7/1991 | Spector . |
| 5,053,002 | 10/1991 | Barlow . |
| 5,171,307 | 12/1992 | Sanning . |

OTHER PUBLICATIONS

Storz Opthalmic Instruments, pp. 241, 264, 1988.

*Primary Examiner*—John D. Yasko
*Attorney, Agent, or Firm*—William Squire

[57] ABSTRACT

A manifold having an array of apertures is secured to one arm of a lid speculum for directing a plurality of sterile saline solution irrigating streams over the cornea during eye surgery. A pressurized fluid source is coupled to the manifold for supplying the fluid. The pressurized source is an IV bottle coupled to a foot operated piston under control of the surgeon during surgery. In a second embodiment, a timer operates an electrical valve for coupling a pressurized source of eye irrigating fluid to the manifold.

19 Claims, 3 Drawing Sheets

EYE SURGERY IRRIGATION DEVICE

This invention relates to systems for irrigating the eye during eye surgery, e.g., cataract surgery.

During eye surgery, for example, cataract or retina surgery, the surgeon typically employs a microscope for observing the surgical site through the cornea and pupil. This requires that the cornea be transparent at all times during the surgery. The transparency is maintained by irrigating the eye during surgery with a saline solution. Presently the way this is handled is for an assistant to stand by the surgeon and periodically spray the saline solution of irrigation fluid over the cornea. This requires the attendance of an additional person which is inefficient.

Generally, irrigation systems or devices for medical use are known. For example, U.S. Pat. No. 5,030,214 discloses an ocular delivery system for dispensing liquid eye treatment solution and includes an eye cup to be placed over the eye, forming a crescent shaped mist of solution and collecting the used solution without contaminating the fresh solution. U.S. Pat. No. 5,053,002 discloses an irrigation system for an angioscope having two flow rates for filling blood vessels under observation with a clear irrigating fluid at a high rate and then switches to a low flow rate. U.S. Pat. No. 5,171,307 discloses an irrigation solution collection device. This device, however, encloses the eye being treated as does the eye cup of the '214 patent discussed above. An eye washing method and apparatus is disclosed also in U.S. Pat. No. 4,798,599. This patent has similar deficiencies noted with the above noted patents in that the critical area of the eye needed to be left open for the surgeon, i.e., the cornea, is covered. Devices which cover the cornea are not useful for concurrent surgical applications for reasons apparent.

The present inventor recognizes a need for an irrigation system that reliably will irrigate the cornea during eye surgery without the need of an assistant.

An irrigation system according to the present invention for irrigating an eye during eye surgery comprises a manifold having a cavity for receiving eye irrigation fluid and having at least one aperture communicating between the manifold cavity and the ambient atmosphere, means for pressurizing the received fluid in the manifold cavity to create at least one stream of the fluid through the aperture and means for securing the manifold adjacent to the eye so that the at least one stream is directed onto the eye cornea during the surgery while leaving the eye substantially obstacle free for the surgery.

In accordance with an embodiment of the present invention, the lids of an eye are spaced apart by a lid speculum during the surgery, the means for securing includes means for securing the manifold to the lid speculum wherein the at least one stream is approximately horizontal with respect to the force of gravity when the speculum is attached to the lids. In a system according to a further embodiment, the means for securing includes means for releasably securing the manifold to the speculum.

Figure 1:
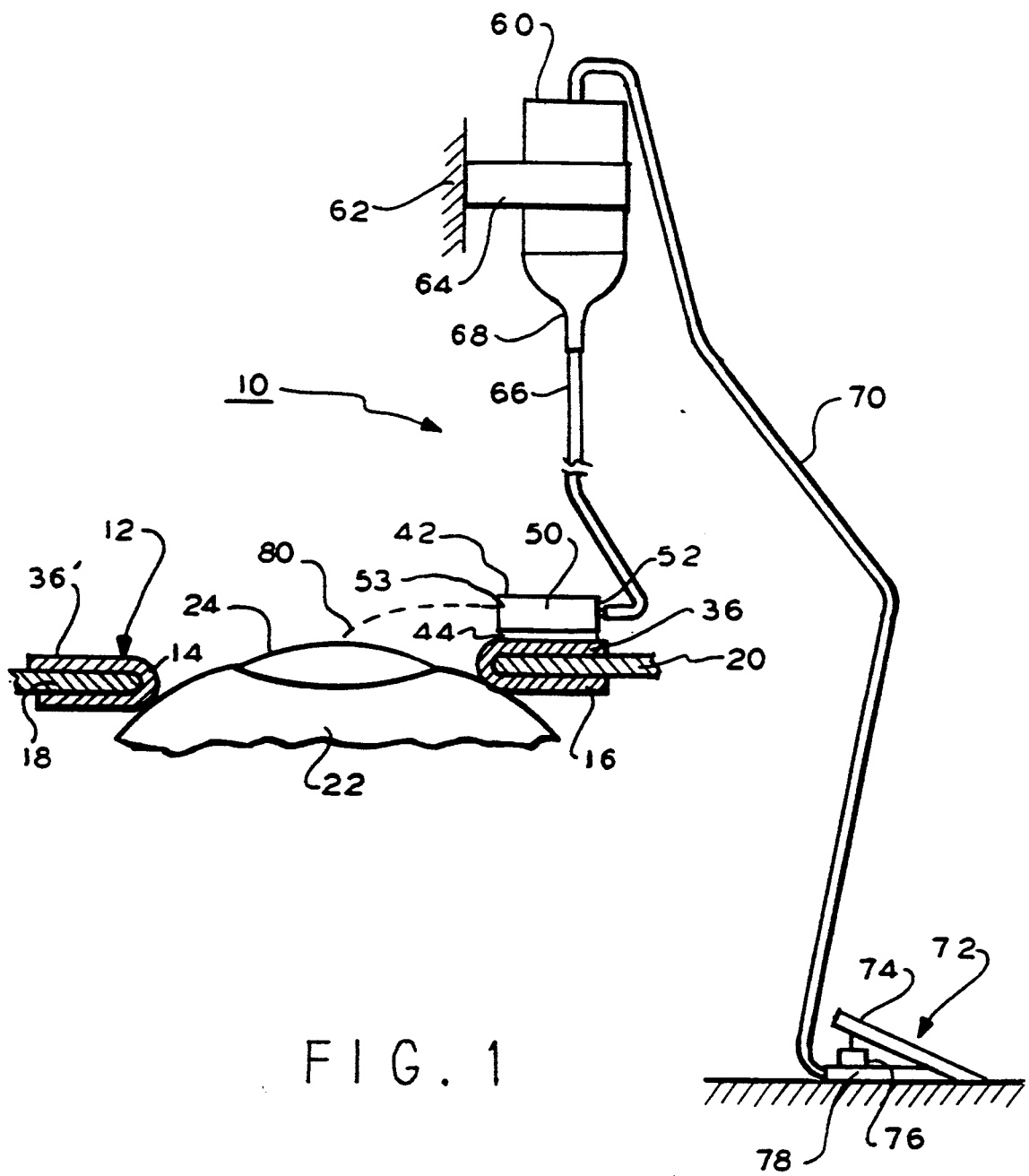
FIG. 1 is a diagrammatic fragmented elevation view partially in section illustrating one embodiment of the present invention.

In FIG. 1, system 10 includes a lid speculum 12 having a pair of lid separating members 14 and 16. The members 14 and 16 separate the lids 18 and 20 of an eye 22 receiving surgery. The cornea 24 of the eye 22 is held open to the ambient atmosphere by the speculum for observation by a microscope (not shown) and for surgical procedures on the cornea 24.

Figure 4:
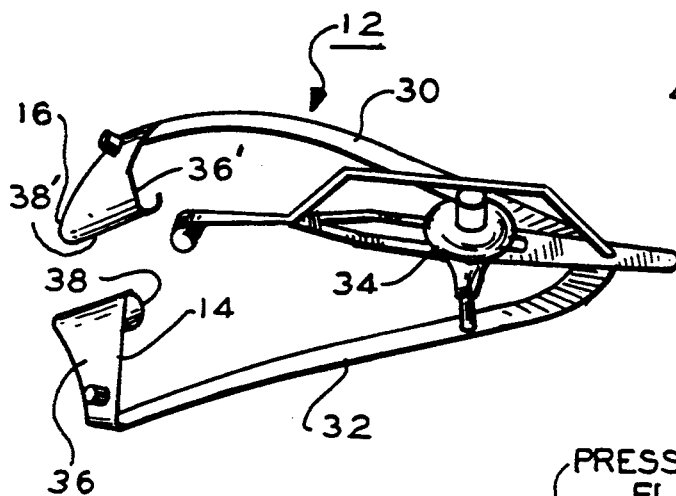
FIG. 4 is a an isometric view of a prior art lid speculum of the type used in the embodiments of FIGS. 1 and 2.

In FIG. 4, the speculum 12 is commercially available and comprises a pair of legs 30 and 32 for respectively securing the members 14 and 16 in the desired spaced position. An adjustment mechanism 34 adjusts the spaced apart position of the members 14 and 16. The members 14 and 16 each comprise a relatively planar blade portion 36 and 36', respectively, and a respective bent portion 38 and 38' for receiving the corresponding lids. The remaining portions of the speculum need not be described herein as they do not form a part of the present invention and are as available commercially.

In FIG. 1, the system 10 includes a manifold 42 which irrigates the eye 22 cornea 24 during surgery to maintain the cornea transparent during surgery for observation by the microscope through the pupil. Manifold 42 receives an irrigation fluid and is secured to planar portion 36 of member 16 (or portion 36 of member 14). The manifold is secured by an adhesive 44 or any other securing device such as Velcro (a commercially available system of hooks and loops) for releasably or permanently securing the manifold to the speculum 12.

Figure 3:
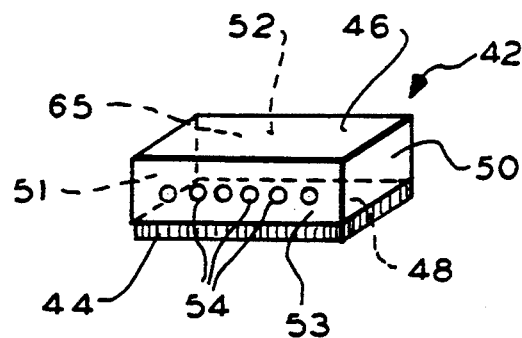
FIG. 3 is an isometric view of a manifold useful in the embodiment of FIGS. 1 and 2.
Figure 3A:
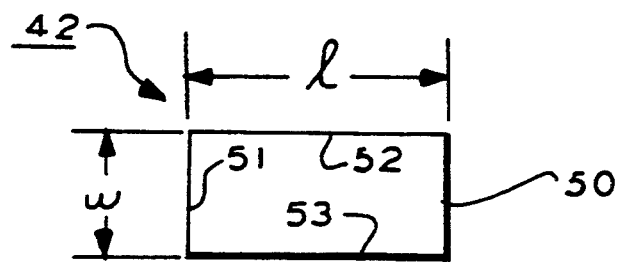
FIG. 3a is a plan view of the manifold of FIG. 3.

In FIG. 3, manifold 42 comprises a thermoplastic molded rectangular polygon having top and bottom walls 46 and 48, respectively, and a plurality of side walls 50, 51, 52 and 53. An array of apertures 54 is formed in side wall 53. The apertures 54 in this embodiment are all of the same diameter and preferably 0.5 mm (0.020 inches) in diameter and spaced 2 mm apart. The apertures may have different diameters in other implementations. While circular, the apertures may be of other shapes. The manifold preferably is 22 mm long along walls 52 and 53, length l, FIG. 3a, and 8 mm wide, width w and 10 mm high, top to bottom of the figure, FIG. 1. The array of apertures preferably includes six apertures, but may include fewer or more according to a given implementation.

In the alternative, the manifold may be a flexible bag-like unit with a plurality of apertures such as apertures 54. The unit may be glued, clipped or otherwise attached by any suitable means to the lid speculum.

In FIG. 1, system 10 further includes an irrigation fluid reservoir container 60 secured above the eye to a support 62 by a bracket 64. The container 60 may be an IV container or any other sterile container. The container may be rigid or flexible. The irrigation fluid stored in the container 60 is preferably a saline solution of water. The container 60 may be rigid or flexible.

Figure 2:
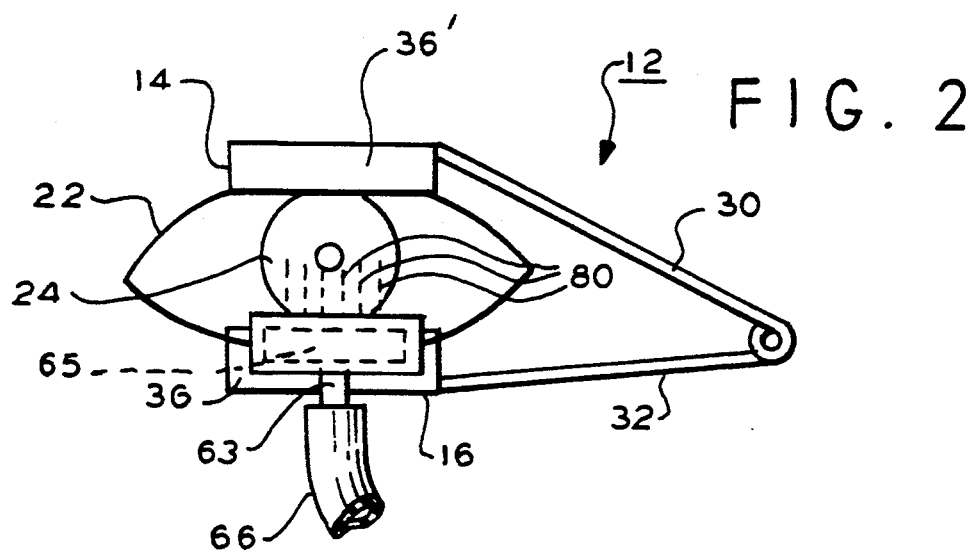
FIG. 2 is a plan view of the eye prior to surgery according to the embodiment of FIG. 1.

A sterile plastic tube 66 couples the mouth 68 of the container 60 via nipple 63, FIG. 2, to the manifold 42 cavity 65. A second thermoplastic tube 70 is coupled between manually operated foot pump 72 and the container 60 cavity 65. The foot pump 72 includes a pedal 74 and a piston 76 secured to a support 78. Depression of the pedal 72 applies pressurized air through tube 70 to the container 60 interior. This pressurizes the irrigation fluid in the container 60. Pump 72 is commercially available.

In operation, the foot pedal 74 is periodically operated by the surgeon during ocular surgery on the eye 22 to pressurize the fluid in container 60. This pressure forces the fluid through tube 66 into manifold 42, filling the manifold cavity 65 and pressurizing the fluid in the manifold cavity. This forces the fluid through the apertures 54 to create a plurality of horizontal streams 80 of saline fluid, FIG. 2, through apertures 54. The streams are directed over the width of the cornea and impinge by gravity onto the cornea somewhat centrally. The fluid then flows by gravity over the entire cornea 24 for maintaining its transparency during the surgery.

As the pressure drops off the surgeon can immediately repressurize the fluid in the manifold while replenishing the manifold to keep the streams flowing continuously. This is important because an assistant doing this irrigation function manually does not know when the surgeon needs more irrigation fluid to maintain the transparency. Thus the surgeon can control the cornea transparency while simultaneously operating on the eye.

Figure 5:
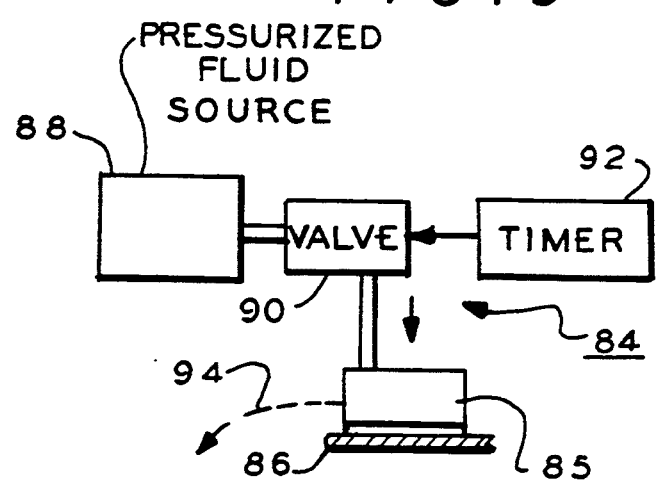
FIG. 5 is a diagrammatic illustration of a system according to a second embodiment of the present invention.

In FIG. 5, an automatic system 84 includes a manifold 85 as described previously. The manifold 85 is secured to lid speculum 86. A source 88 of pressurized fluid, which may include any suitable sterile container and a system for pressurizing the fluid in the container using a pressure regulator (not shown). The pressurized fluid is coupled to manifold 85 via an electrically operated valve 90 controlled by a timer 92. The timer 92 periodically opens and closes the valve to provide sufficient fluid to the manifold to maintain the presence of the irrigation streams 94. The period of the timer is such so as to keep the cornea moist and transparent at all times. This period can be established empirically according to a given implementation. There are available sponge-like devices which are used to drain excessive irrigation fluid from the eye during irrigation. Therefore, the amount of fluid used to irrigate the cornea is not critical. The length of the streams is not critical as long as the cornea is irrigated to obtain the desired transparency.

Figure 6:
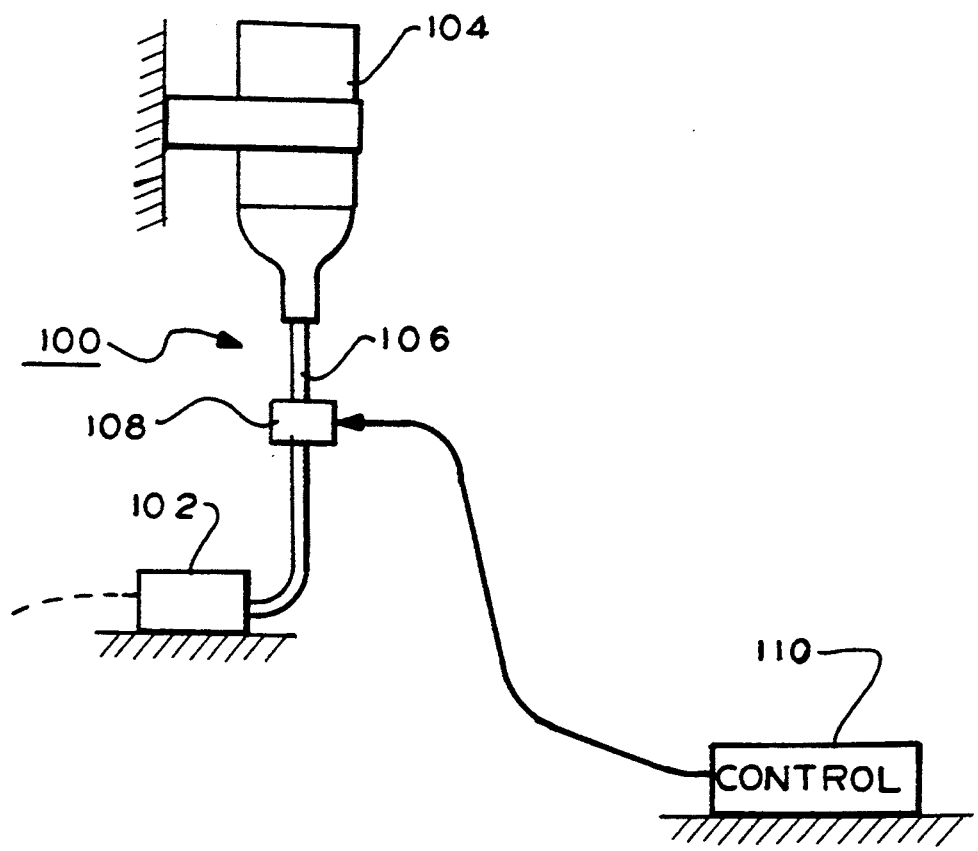
FIG. 6 is a diagrammatic view similar to that of FIG. 1 illustrating a further embodiment of the present invention.

In FIG. 6, an alternative embodiment is disclosed in which system 100 comprises a manifold 102 as previously described. In this system a container 104 of irrigation fluid is suspended above the manifold and feeds the irrigation fluid by gravity to the manifold through tube 106. An electrically operated valve 108 is operated by a control 110, such as an electrical timer or manually operated switch coupled to a power source (not shown) to periodically supply the irrigation fluid to the manifold 102.

In all of the embodiments the amount of pressure needed to supply the manifold and maintain the fluid streams can be determined empirically for a given implementation. For example, the pressure of the source may be varied or the valve controlling the frequency of the application of the pressure to the fluid may be cycled opened and closed with a controllable duty cycle to obtain the desired streams. Also, any combination of factors such as pressure, aperture size, duty cycle and so on may be varied to obtain the desired stream effects. The position of the apertures in the manifold also is not critical, but should be so positioned that sufficient fluid is in the manifold to maintain the streams. Thus it is preferable the apertures are nearer to the bottom wall of the manifold as compared to the top wall.

While particular embodiments have been described, it will occur to one of ordinary skill that various modifications may be made to the described embodiments. The disclosed embodiments are given by way of illustration and not limitation. The scope of the invention is defined by the appended claims.

What is claimed is:

1. Irrigation system for irrigating an eye during surgery, the system comprising:
   a manifold having a cavity for receiving eye irrigation fluid and having at least one aperture communicating between the manifold cavity and the ambient atmosphere;
   means for pressurizing the received fluid in said manifold cavity to create at least one stream of said fluid through the aperture; and
   means for securing the manifold adjacent to the eye so that the at least one stream is directed onto the eye cornea during the surgery while leaving the eye substantially obstacle free for the surgery.

2. The system of claim 1 wherein the lids of an eye are spaced apart by a lid speculum during the surgery, the means for securing including means for securing the manifold to the lid speculum wherein the at least one stream is approximately horizontal with respect to the force of gravity when the speculum is attached to the lids.

3. The system of claim 2 wherein the means for securing includes means for releasably securing the manifold to the speculum.

4. The system of claim 2 wherein the manifold has top and bottom walls and a plurality of side walls, said at least one aperture being formed in one of said side walls, said means for securing the bottom wall to said speculum.

5. The system of claim 1 wherein the manifold includes a plurality of apertures facing in the same general direction.

6. The system of claim 5 wherein the plurality of apertures are about the same diameter.

7. The system of claim 2 wherein the fluid is water and the pressure in the manifold and the aperture size are such that the stream impinges generally on the cornea with the manifold secured to said speculum.

8. The system of claim 1 wherein the means for pressurizing includes a manually operated pump coupled to the manifold.

9. The system of claim 8 wherein the pump is foot operated.

10. The system of claim 1 wherein the means for pressurizing includes timing means and a pressurized source of said fluid coupled to the timing means for periodically automatically pressurizing said manifold.

11. The system of claim 1 wherein the at least one aperture comprises a plurality of apertures each about 0.020 inches in diameter facing in the same general direction and the fluid is a saline solution.

12. The system of claim 1 including timing means for repetitively spraying the at least one stream in the range of 1–5 seconds.

13. The system of claim 1 wherein the means for pressurizing the fluid includes a container of said fluid and means for securing the container to gravity feed fluid from the container to said manifold and electrically operated control means for selectively periodically coupling the fluid from the container to said manifold.

14. Irrigation system for irrigating an eye during surgery, the eye being held open by a lid speculum which spaces the lids apart, the system comprising:
   a manifold having a cavity for receiving eye irrigation fluid and having a plurality of apertures each communicating between the manifold cavity and the ambient atmosphere in a given direction;
   means for pressurizing the received fluid in said manifold cavity to create a stream of said fluid through each of the apertures; and
   means for securing the manifold to the speculum adjacent to the eye so that the streams are directed generally horizontally relative to the force of gravity onto the eye cornea during the surgery.

15. The system of claim 15 wherein the speculum includes a pair of spaced lid gripping members, the system including means for securing the manifold to one of said members.

16. The system of claim 14 wherein the manifold is molded thermoplastic.

17. The system of claim 14 wherein the means for pressurizing includes means for periodically applying pressure to said fluid in said manifold.

18. The system of claim 17 wherein said means for periodically applying pressure includes electrical control means.

19. The system of claim 17 wherein said means for periodically applying pressure includes manual pump means.

* * * * *